United States Patent [19]

Bargiotti et al.

[11] Patent Number: 4,672,057
[45] Date of Patent: Jun. 9, 1987

[54] MORPHOLINO DERIVATIVES OF DAUNORUBICIN AND DOXORUBICIN

[75] Inventors: Alberto Bargiotti, Milan; Pierangelo Zini, Cesano Boscono; Sergio Penco, Milan; Fernando Giuliani, Cassina De Pecchi, all of Italy

[73] Assignee: Farmitalia Carlo ERBA S.p.A., Milan, Italy

[21] Appl. No.: 839,936

[22] Filed: Mar. 17, 1986

[30] Foreign Application Priority Data

Mar. 22, 1985 [GB] United Kingdom ............... 8507577

[51] Int. Cl.⁴ .................... A61K 31/70; C07H 15/24
[52] U.S. Cl. ........................................ 514/34; 536/6.4
[58] Field of Search ........................... 536/6.4; 514/34

[56] References Cited

U.S. PATENT DOCUMENTS 4,464,529 8/1984 Mosher et al. .................... 536/6.4

Primary Examiner—Johnnie R. Brown
Assistant Examiner—Elli Peselev
Attorney, Agent, or Firm—Oblon, Fisher, Spivak, McClelland & Maier

[57] ABSTRACT

Anthracycline glycosides of the general formula (A):

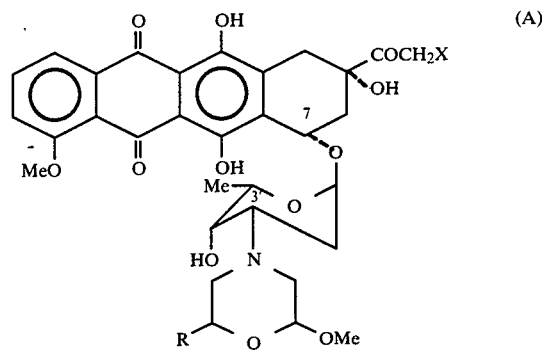

wherein X is hydrogen or hydroxy and R is hydrogen or a methyl or a hydroxymethyl group; and their pharmaceutically acceptable salts; are useful as antitumor agents.

9 Claims, No Drawings

MORPHOLINO DERIVATIVES OF DAUNORUBICIN AND DOXORUBICIN

The present invention relates to anthracycline antitumor glycosides, methods for their preparation, compositions containing them and the use of the compounds.

Daunorubicin (daunomycin) and doxorubicin (adriamycin) are both well-known anthracycline antitumor glycosides, and both their preparation and use are amply described in the prior art. Daunomycinone, the aglycone of daunorubicin, which is one of the starting material used in the preparation of the compounds of the invention is also a well known material and is described and claimed in British Pat. No. 1,003,383.

The present invention provides, in one aspect thereof, a new class of anthracycline glycoside antibiotics of the formula (A):

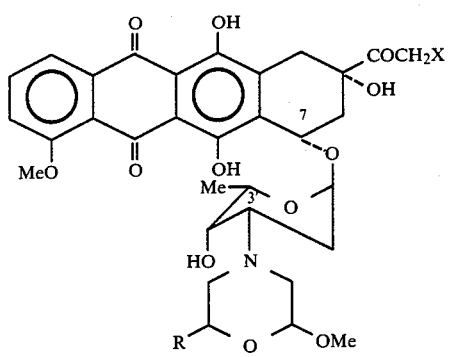

(A)

wherein X is hydrogen or hydroxy and R is hydrogen or a methyl or hydroxymethyl group and pharmaceutically acceptable salts thereof such as the hydrochloride. More particularly the new anthracycline glycosides are:

I: 3'-deamino-3'-(2"-methoxy-4"-morpholinyl)-daunorubicin (X=R=H)
II: 3'-deamino-3'-(2"-methoxy-4"-morpholinyl)doxorubicin (R=H; X=OH)
III: 3'-deamino-3'-(2"-methoxy-6"-methyl-4"-morpholinyl)daunorubicin (R=CH$_3$; X=H)
IV: 3'-deamino-3'-(2"-methoxy-6"-methyl-4"-morpholinyl)doxorubicin (R=CH$_3$; X=OH)
V: 3'-deamino-3'-(2"-methoxy-6"-hydroxymethyl-4"-morpholinyl)daunorubicin (R=CH$_2$OH; X=H)
VI: 3'-deamino-3'-(2"-methoxy-6"-hydroxymethyl-4"-morpholinyl)doxorubicin (R=CH$_2$OH; X=OH)

The compounds of formula (A) are prepared by the formation of a substituted morpholinyl ring at C-3' on the sugar moiety of the anthracyclines daunorubicin and doxorubicin through a reductive alkylation, based on using a chiral dialdehyde of the general formula (B), wherein R represents a hydrogen atom or a methyl or a hydroxymethyl group.

(B)

Accordingly, the present invention provides a process for the preparation of an anthracycline glycoside of formula (A) as defined in claim 1 or a pharmaceutically acceptable salt thereof, which process comprises reacting daunorubicin or doxorubicin or an acid addition salt thereof with an excess of an aldehyde of formula (B) in the presence of an alkali metal cyanoborohydride and, if desired, converting a compound of formula (A) thus obtained into a pharmaceutically acceptable salt thereof.

The reductive alkylation is typically carried out using an excess of the dialdehyde in a mixed aqueous polar organic medium, such as water-acetonitrile, generally at a pH of about 7 in presence of an alkali metal cyanoborohydride e.g. sodium or potassium cyanoborohydride. The reaction can be usually completed in two hours at room temperature. The desired product is isolated from the reaction mixture by solvent extraction and purified by column chromatography.

For example, to obtain a hydrochloride of the invention daunorubicin or doxorubicin, in the form of its hydrochloride, is dissolved in a mixture of acetonitrile-water (1:1 v/v) and, after having adjusted the pH to 7.4 with an aqueous solution of sodium hydrogen carbonate, is reacted at room temperature with an excess (7–10 equiv.) of a dialdehyde of formula (B):

(B)

wherein R represents a hydrogen atom or a methyl or a hydroxymethyl group, in the presence of an aqueous solution of NaBH$_3$CN in an equivalent amount with respect to the starting daunorubicin to obtain, after a 15 minutes stirring at room temperature, the raw glycoside compound of formula (A) (X=H or OH) which, after purification by flash chromatography on silica gel column using as eluting system methylene dichloride-acetone (96:5 v/v) is isolated as its hydrochloride.

A dialdehyde of formula (B) is prepared via a Malaprade reaction on the methyl glycoside of a sugar in pyranic form. More particularly, this is achieved by periodic acid oxidation of the methylglycoside of:
(i) arabinose in pyranic form to afford the dialdehyde (BI) (R=H)
(ii) rhamnose affords (BII) (R=Me)
(iii) glucose affords (BIII) (R=CH$_2$OH)

Moreover the invention provides pharmaceutical compositions comprising an anthracycline glycoside of the formula (A) or a pharmaceutically acceptable salt thereof in combination with a pharmaceutically acceptable diluent or carrier. These compositions contain a therapeutically effective amount of the glycoside or its salt. The invention additionally provides methods of using the glycosides or their salts in treating certain mammalian tumors by administering a therapeutically effective amount to a patient.

The following Examples illustrate the invention.

EXAMPLE 1

Preparation of 1-methoxy-2,2'-oxydiacetaldehyde (BI)

A solution of methyl-α-L-arabinopyranoside (1.64 g, 10 mmol) in water (25 ml) was treated in portions with sodium periodate (4.3 g) at 0° C. After 3 hours, the iodate and excess periodate were precipitated by addition of a solution of barium chloride. The mixture was neutralized (BaCO$_3$) and filtered, the insoluble material being washed with water. To the filtrate ethanol was added and set aside overnight in the refrigerator to precipitate inorganic material. After filtration, the solution was concentrated to a syrup that was extracted with acetonitrile (10 ml). The extract was used for the next step without further purification.

EXAMPLE 2

Preparation of 3'-deamino-3'-(2''-methoxy-4''-morpholinyl)daunorubicin (I)

To a solution of daunorubicin hydrochloride (0.57 g, 1 mmol) in 40 ml of acetonitrile-water (1:1) was added the solution of dialdehyde prepared as described in example 1. The pH was adjusted to 7.4 with a solution of sodium hydrogen carbonate. After 2 hours the stirred mixture was treated with a solution of 0.064 (1 mmol) of NaBH$_3$CN in 5 ml of water. After 15 minutes the mixture was worked up by dilution with water (100 ml) and extraction with methylene chloride. The organic phase was evaporated under vacuum. The resulting residue is purified by flash chromatography on silica gel column using methylene dichloride:acetone (96:5 v/v) as the eluting system. There are obtained 0.360 g (yield 55%) of I that was isolated as hydrochloride. m.p. 160°–161° C.

NMR (200 MHz, CDCl$_3$): 13.98 (s, 1H, OH-6), 13.28 (s, 1H, OH-11), 8.02 (d, J=8.0 Hz, 1H, H-1), 7.77 (t, J=8.0 Hz, 1H, H-2), 7.38 (d, J=8.0 Hz, 1H, H-3), 5.54 (m, 1H, H-1'), 5.26 (dd, J=2.2, 4.2 Hz, 1H, H-7), 4.64 (s, 1H, OH-9), 4.49 (dd, J=2.6, 4.0 Hz,

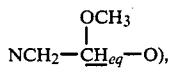

4.07 (s, 3H, OCH$_3$-4), 4.01 (dq, J=1.0, 6.5 Hz, 1H, H-5'), 3.90 (m, 1H, NH$_2$-CH(H)O), 3.65 (m, 1H, H-4'), 3.4–3.6 (m, 1H, NCH$_2$-CH(H)O), 3.38 (s, 3H, OCH$_3$—CHCH$_2$N), 3.21 (dd, J=1.8, 19.0 Hz, 1H, H-10e), 2.93 (d, J=19.0 Hz, 1H, H-10ax), 2.61 (dd, J=4.0, 11.4 Hz, NCH$_e$(H)—CHOCH$_3$), 2.3–2.5 (m, 3H, H-8e, H-3', NCH$_{ax}$(H)—CHOCH$_3$), 2.40 (s, 3H, CH$_3$-14), 2.08 (dd, J=4.2, 15.0 Hz, 1H, H-8ax), 1.7–1.8 (m, 2H, CH$_2$-2'), 1.36 (d, J=6.5 Hz, 3H, CH$_3$-5').

EXAMPLE 3

Preparation of 3'-deamino-3'-(2''-methoxy-4''-morpholinyl)-doxorubicin (II)

The synthesis of the compound II starting from doxorubicin hydrochloride (0.58 g, 1 mmol) and the 1-methoxy-2,2-oxybisacetaldehyde solution of Example 1 was performed according to the procedure described in Example 2. 3'-Deamino-3'-(2''-methoxy-4''-morpholinyl)doxorubicin (II) was obtained as the hydrochloride in an amount of 0.38 g (yield 55%) m.p. 163°–164° C.

NMR (200 MHz, CDCl$_3$): 13.97 (s, 1H, OH-6), 13.26 (s, 1H, OH-11), 8.03 (dd, J=1.2, 8.0 Hz, 1H, H-1), 7.78 (t, J=8.0 Hz, 1H, H-2), 7.40 (dd, J=1.2, 8.0 Hz, 1H, H-3), 5.55 (, J=2.6 Hz, 1H, H-1'), 5.29 (dd, J=2.2, 3.9 Hz, 1H, H-7), 4.74 (d, J=3.0 Hz, 2H, CH$_2$OH-14), 4.49 (dd, J=2.5, 4.0 Hz,

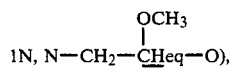

4.08 (s, 3H, OCH$_3$-4), 3.93 (dq, J=6.5, 1.0 H, 1H, H-5'), 3.92 (m, 1H, NCH$_2$CH(H)O), 3.67 (dd, J=2.0, 1.0 Hz, 1H, H-4'), 3.54 (m, 1H, NCH$_2$CH(H)O), 3.38 (s, 3H, NCH$_2$—CH—OCH$_3$), 3.26 (dd, J=1.7, 19.0 Hz, 1H, H-10e), 3.00 (d, J=19.0 Hz, 1H, H-10ax), 2.60 (dd, J=4.0, 11.4 Hz, 1H,

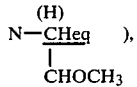

2.47 (m, 2H, NCH$_2$CH$_2$O), 2.45 (m, 1H,

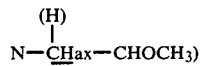

2.3–2.4 (m, 1H, H-8e), 2.34 (m, 1H, H-3'), 2.14 (dd, J=3.9, 15.0 Hz, H-8ax), 1.76 (m, 2H, CH$_2$-2'), 1.36 (d, J=6.5 Hz, 3H, CH$_3$-5').

EXAMPLE 4

Preparation of 1-methyl-1'-methoxy-2,2'-oxydiacetaldehyde (BII)

A solution of methyl-α-L-rhamnopyranoside (1.78 g, 10 mmol) in water (25 ml) was treated with sodium periodate (4.3 g) at 0° C. After 3 hours sodium hydrogen carbonate was cautiously added to neutralize the acid, the mixture was poured into ethanol (100 ml) and the insoluble material was filtered. The filtrate was concentrated to a syrup that was extracted with acetonitrile (15 ml). The extract was used for the next step without further purification.

EXAMPLE 5

Preparation of 3'-deamino-3'-(2''-methoxy-6''-methyl-4''-morpholinyl)-daunorubicin (III)

The synthesis of the compound III starting from daunorubicin hydrochloride (0.57 g, 1 mmol) and the 1-methyl-1'-methoxy-2,2'-oxydiacetaldehyde solution of Example 4 was performed according to the procedure described in Example 2. 3'-Deamino-3'-(2''-methoxy-6''-methyl-4''-morpholinyl)daunorubicin was isolated as the hydrochloride in an amount of 0.34 g (yield 50%) m.p. 152° C.

NMR (200 MHz, CDCl$_3$): 13.97 (s, 1H, OH-6), 13.29 (s, 1H, OH-11), 8.02 (dd, J=1.2, 8.0 Hz, 1H, H-1), 7.77 (t, J=8.0 Hz, 1H, H-2), 7.39 (dd, J=1.2, 8.0 Hz, 1H, H-3), 5.53 (m, 1H, H-1'), 5.26 (dd, J=2.0, 4.0 Hz, 1H, H-7), 4.67 (s, 1H, OH-9), 4.59 (bd, J=2.0 Hz, 1H,

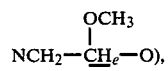

4.08 (s, 3H, OCH$_3$-4), 3.9–4.0 (m, 1H,

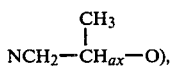

4.00 (dq, J=1.5, 6.6 Hz, 1H, H-5'), 3.71 (m, 1H, H-4'), 3.34 (s, 3H,

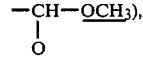

3.21 (dd, J=2.0, 19.2 Hz, H-10$_e$) 2.93 (d, J=19.2 Hz, 1H, H-10$_{ax}$), 2.95 (bd, J=11.0 Hz, 1H,

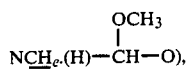

2.83 (bd, J=11.5 Hz, 1H,

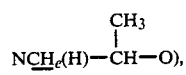

2.40 (s, 3H, CH$_3$-14), 2.35 (ddd, J=2.0, 2.0, 15.0 Hz, 1H, H-8$_e$), 2.17 (dd, J=2.8, 11.5 Hz, 1H,

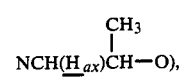

2.07 (dd, J=4.0, 15.0 Hz, 1H, H-8$_{ax}$), 1.82 (dd, J=11.0, 11.0 Hz, 1H,

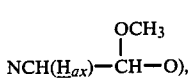

1.7–1.8 (m, 2H, CH$_2$-2'), 1.36 (d, J=6.6 Hz, 3H, CH$_3$-5'), 1.09 (d, J=6.2 Hz, 3H,

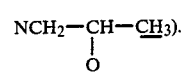

EXAMPLE 6

Preparation of 3'-deamino-3'-(2''-methoxy-6''-methyl-4''-morpholinyl)-doxorubicin (IV)

The synthesis of the compound (IV) starting from doxorubicin hydrochloride (0.56 g, 1 mmol) and the 1-methyl-1'-methoxy-2,2'-oxydiacetaldehyde solution of Example 4 was performed according to the procedure described in Example 2. 3'-Deamino-3'-(2''-methoxy-6''-methyl-4''-morpholinyl)-doxorubicin (IV) was isolated as the hydrochloride in an amount of 0.35 g (yield 51%) m.p. 162° C.

NMR (200 MHz, CDCl$_3$): 13.88 (s, 1H, OH-6), 13.15 (s, 1H, OH-1'), 7.97 (dd, J=1.0, 8.0 Hz, 1H, H-1), 7.76 (t, J=8.0 Hz, 1H, H-2), 7.37 (dd, J=1.0, 8.0 Hz, 1H, H-3), 5.53 (m, 1H, H-1'), 5.30 (dd, J=2.1, 4.0 Hz, 1H, H-7), 4.74 (s, 2H, CH$_2$OH-14), 4.60 (bd, J=2.3 Hz, 1H,

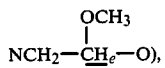

4.08 (s, 3H, OCH$_3$-4), 4.00 (m, 1H,

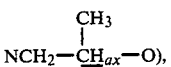

3.92 (dq, J=1.0, 6.5 Hz, 1H, H-5'), 3.71 (m, 1H, H-4'), 3.34 (s, 3H,

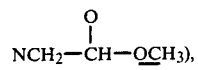

3.27 (dd, J=1.5, 19.0 Hz, 1H, H-10$_e$), 3.03 (d, J=19.0 Hz, 1H, H-10$_{ax}$), 2.97 (bd, J=11.5 Hz, 1H,

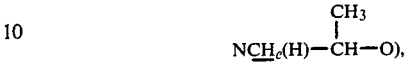

2.82 (bd, J=11.5 Hz, 1H,

2.1–2.4 (m, 4H, CH$_2$-8, H-3,

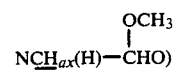

1.83 (dd, J=11.5, 11.5 Hz, 1H,

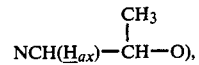

1.75 (m, 2H, CH$_2$-2'), 1.36 (d, J=6.5 Hz, 3H, CH$_3$-5'), 1.10 (d, J=6.5 Hz, 3H,

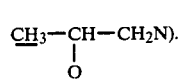

EXAMPLE 7

Preparation of 1-hydroxymethyl-1'-methoxy-2,2'-oxydiacetaldehyde (BIII)

A solution of methyl-α-D-glucopyranoside (1.95 g, 10 mmol) in 20 ml of water was treated in portions with sodium periodate (4.3 g) at 0° C. A olution of the 1-hydroxymethyl-1'-methoxy-2,2'-oxydiacetaldehyde thus-prepared was obtained by the procedure described in Example 1.

EXAMPLE 8

Preparation of 3'-deamino-3'-(2''-methoxy-6''-hydroxymethyl-4''-morpholinyl)-daunorubicin (V)

The synthesis of the compound (V) starting from daunorubicin hydrochloride (0.57 g, 1 mmol) and the 1-hydroxymethyl-1'-methyl-2,2'-oxydiacetaldehyde solution of Example 7 was performed according to the procedure described in Example 2. 3'-Deamino-3'-(2''-methoxy-6''-hydroxymethyl-4''-morpholinyl)-daunorubicin (V) was isolated as the hydrochloride in an amount of 0.35 g (yield 50%) m.p. 164° C.

NMR (200 MHz, CDCl$_3$): 13.98 (s, 1H, OH-6), 13.28 (s, 1H, OH-11), 8.02 (dd, J=1.0, 8.0 Hz, 1H, H-1), 7.78 (t, J=8.0 Hz, 1H, H-2), 7.38 (dd, J=1.0, 8.0 Hz, 1H, H-3), 5.54 (m, 1H, H-1'), 5.28 (dd, J=2.0, 4.0 Hz, 1H, H-7), 4.66 (bs, 1H,

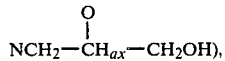

4.63 (s, 1H, OH-9), 4.08 (s, 3H, OCH₃-4), 4.02 (dq, J=2.0, 6.5 Hz, 1H, H-5'), 3.95–4.05 (m, 1H,

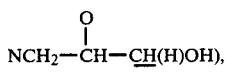

3.67 (m, 1H, H-4'), 3.65 (dd, J=3.0, 12.0 Hz, 1H,

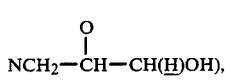

3.55 (dd, J=5.0 12.0 Hz, 1H,

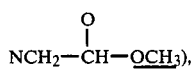

3.34 (s, 3H,

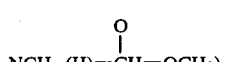

3.33 (dd, J=1.0, 19.0 Hz, 1H, H-10$_e$), 3.08 (bd, J=11.0 Hz, 1H,

2.95 (d, J=19.0 Hz, 1H, H-10ax), 2.75 (bd, J=11.0 Hz, 1H,

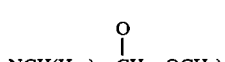

2.40 (s, 3H, CH₃-1H), 2.3–2.45 (m, 2H, H-3', H-8$_e$), 2.17 (dd, J=4.0, 13.0 Hz, 1H, H-8$_{ax}$), 2.15 (m, 1H,

2.07 (dd, J=11.0, 11.0 Hz, 1H,

NCH(H$_{ax}$)—CH—CH₂OH), 1.79 (m, 2H, CH₂-2'), 1.36 (d, J=6.5 Hz, 3H, CH₃-5').

EXAMPLE 9

Preparation of 3'-deamino-3'-(2''-methoxy-6''-hydroxymethyl-4''-morpholinyl)-doxorubicin (VI)

The synthesis of the compound VI starting from doxorubicin hydrochloride (0.58 g, 1 mmol) and the 1-hydroxymethyl-1'-methyl-2,2'-oxydiacetaldehyde solution of Example 7 was performed according to the procedure described in Example 2. 3'-Deamino-3'-(2''-methoxy-6''-hydroxymethyl-4''-morpholinyl)-doxorubicin (VI) was isolated as hydrochloride in an amount of 0.36 g (yield 51–52%) m.p. 165° C.

NMR (200 MHz, CDCl₃): 13.92 (s, 1H, OH-6), 13.17 (s, 1H, OH-11), 7.99 (d, J=8.0 Hz, 1H, H-1), 7.76 (t, J=8.0 Hz, 1H, H-2), 7.38 (d, J=8.0 Hz, 1H, H-3), 5.52 (m, 1H, H-1'), 5.25 (m, 1H, H-7), 4.73 (s, 2H, CH₂OH-14), 4.70 (s, 1H, OH-9), 4.66 (bs, 1H,

4.06 (s, 3H, OCH₃-4), 3.9–4.0 (m, 1H,

3.92 (dq, J=2.0, 6.5 Hz, 1H, H-5'), 3.68 (m, 1H, H-4'), 3.61 (dd, J=4.0, 11.5 Hz, 1H,

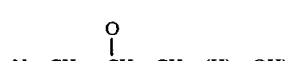

3.51 (dd, J=5.5, 11.5 Hz, 1H,

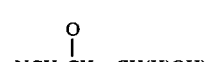

3.33 (s, 3H, NCH₂CH-OCH₃), 3.20 (dd, J=1.0, 19.0 Hz, 1H, H-10$_e$), 3.00 (bd, J=11.0 Hz, 1H,

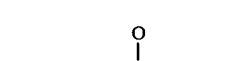

2.93 (d, J=19.0 Hz, 1H, H-10$_{ax}$), 2.73 (bd, J=11.0 Hz, 1H,

2.3–2.5 (m, 2H, H-3', H-8$_e$), 2.20 (dd, J=4.0, 13.0 Hz, 1H, H-8$_{ax}$), 2.15 (dd, J=3.0, 11.0 Hz, 1H,

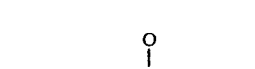

2.04 (dd, J=11.0, 11.0 Hz, 1H,

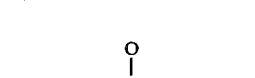

1.80 (m, 2H, CH₂-2'), 1.35 (d, J=6.5 Hz, 3H, CH₃-5').

BIOLOGICAL ACTIVITY OF I–VI

The compounds have been tested in several experimental systems in order to ascertain their cytotoxicity and antitumor activity in experimental animals. Data reported in Table I show that all the compounds are more cytotoxic than the parent drugs daunorubicin and doxorubicin.

The primary screening in vivo was carried out in CDF-1 mice bearing P388 ascetic leukemia (10⁶ cells/- mouse). Results are reported in Table II. All the compounds are active, in particular compound V is more active than daunorubicin giving at the same optimal dose a higher increase of the mice life span. The doxorubicin analogs II, IV and VI are more potent than the parent drug. In particular II is 60 times more potent and exhibits a major efficacy (T/C % 295). The doxorubicin analogs II, IV, VI have been tested in C3H mice bearing the Gross leukemia injected iv ($2 \times 10^6$ cell/mouse). Data are reported in Table III. Administered iv on day 1 after the tumor inoculation, the compounds were more potent than doxorubicin. Compound II has been studied on P388 leukemia cells resistant to doxorubicin (P388/DX) in vitro and in vivo. Cytotoxicity tests were carried out exposing the cells to various drug concentrations for 48 hrs. At the end of exposure period cells were counted with a coulter cell counter, and the $ID_{50}$ (dose which gives 50% reduction of the cell number in comparison with untreated controls) was calculated. Results reported in Table IV show that II was 40 times more cytotoxic than doxorubicin on P388 leukemia cells and was very active also on P388/DX leukemia cells while doxorubicin on this line is obviously inactive. Compound II has been tested also in vivo in BDF-1 mice bearing P388/DX leukemia. The data reported in Table V show that the compound at 0.15 mg/Kg is very active (T/C % 165).

TABLE I

Colony inhibition test against HeLa cells in vitro (treatment for 24 hrs)

| COMPOUND | $ID_{50}$ (ng/ml) |
|---|---|
| DAUNORUBICIN | 18.6 |
| I | 2.0 |
| III | 1.8 |
| V | 10.5 |
| DOXORUBICIN | 18 |
| II | 0.96 |
| IV | 0.32 |
| VI | 9.0 |

TABLE II

Antitumor activity against P388 leukemia treatment ip on day 1

| Compound | Dose (mg/Kg) | T/C %[a] | LTS[b] | Toxic deaths[c] |
|---|---|---|---|---|
| DAUNORUBICIN | 2.9 | 145 | 0/10 | 0/10 |
|  | 4.4 | 150 | 0/10 | 1/10 |
| I | 0.13 | 136 | 0/10 | 0/10 |
| V | 2.0 | 145 | 0/10 | 0/10 |
|  | 3.0 | 164 | 0/10 | 0/10 |
| DOXORUBICIN | 6.6 | 214 | 0/10 | 0/10 |
|  | 10 | 214 | 1/10 | 0/10 |
| II | 0.15 | 295 | 2/10 | 0/10 |
| IV | 0.2 | 173 | 0/10 | 0/10 |
| VI | 1.33 | 164 | 0/10 | 0/10 |
|  | 2 | 195 | 0/10 | 0/10 |

[a]Median survival time; % over untreated controls
[b]Long term survivors (>60 days)
[c]Evaluated on the basis of autopsy findings on dead mice

TABLE III

Activity on Gross leukemia (IV-1)

| Compound | Dose (mg/Kg) | T/C %[a] | LTS[b] | Toxic deaths[c] |
|---|---|---|---|---|
| DOXORUBICIN | 10 | 183 | 0/10 | 0/10 |
|  | 13 | 200 | 0/10 | 0/10 |
| II | 0.16 | 150 | 0/10 | 0/10 |
| IV | 0.27 | 142 | 0/10 | 0/10 |
| VI | 2 | 150 | 0/10 | 0/10 |

[a,b,c]see Table II

TABLE IV

Effect on sensitive and doxorubicin-resistant P388 Leukemia in vitro

| Compound | $ID_{50}$ (ng/ml)[a] P388[b] | P388/DX[c] |
|---|---|---|
| Doxorubicin | 12 | 1500 |
| II | 0.3 | 3 |

[a]Dose giving 50% reduction of cell number in comparison with untreated controls
[b]P388 leukemia cells sensitive to doxorubicin
[c]P388 leukemia cells resistant to doxorubicin

TABLE V

Effect on doxorubicin-resistant P388 leukemia in vivo

| Compound | dose (mg/Kg) | T/C[a] | LTC[b] | Toxic[c] deaths |
|---|---|---|---|---|
| Doxorubicin | 4.4 | 110 | 0/10 | 0/10 |
|  | 6.6 | 100 | 0/10 | 0/10 |
| II | 0.075 | 100 | 0/10 | 0/10 |
|  | 0.15 | 165 | 0/10 | 1/10 |

[a,b,c]see Table II

We claim:

1. An anthracycline glycoside of the formula A:

(A)

[Chemical structure diagram of anthracycline glycoside with COCH₂X, OH, MeO, Me, HO, N, R, OMe substituents]

wherein X is hydrogen or hydroxy and R is hydrogen or a methyl or a hydroxymethyl group; or pharmaceutically acceptable salts thereof.

2. A compound according to claim 1, which is 3'-deamino-3'-(2''-methoxy-4''-morpholinyl)-daunorubicin or its hydrochloride salt.

3. A compound according to claim 1, which is 3'-deamino-3'-(2''-methoxy-4''-morpholinyl)doxorubicin or its hydrochloride salt.

4. A compound according to claim 1, which is 3'-deamino-3'-(2''-methoxy-6''-methyl-4''-morpholinyl)-daunorubicin or its hydrochloride salt.

5. A compound according to claim 1, which is 3'-deamino-3'-(2''-methoxy-6''-methyl-4''-morpholinyl)-doxorubicin or its hydrochloride salt.

6. A compound according to claim 1, which is 3'-deamino-3'-(2''-methoxy-6''-hydroxymethyl-4''-morpholinyl)-daunorubicin or its hydrochloride salt.

7. A compound according to claim 1, which is 3'-deamino-3'-(2''-methoxy-6''-hydroxymethyl-4''-morpholinyl)-doxorubicin or its hydrochloride salt.

8. A pharmaceutical composition comprising an effective amount of an anthracycline glycoside or a pharmaceutically acceptable salt thereof as claimed in any one of claims 1 to 7 in admixture with a pharmaceutically acceptable diluent or carrier, for treatment of P388 leukemia or Gross leukemia.

9. A method of treating P388 leukemia or Gross leukemia in a subject in need of such treatment, which comprises administering to the subject an effective amount of an anthracycline glycoside or a pharmaceutically acceptable salt thereof as claimed in any one of claims 1 to 7.

* * * * *